United States Patent [19]

Stevens

[11] 4,149,635
[45] Apr. 17, 1979

[54] STRIP TRAY

[75] Inventor: Frank W. Stevens, Rutherford, N.J.

[73] Assignee: Becton, Dickinson and Company, East Rutherford, N.J.

[21] Appl. No.: 818,076

[22] Filed: Jul. 22, 1977

Related U.S. Application Data

[63] Continuation of Ser. No. 692,357, Jun. 3, 1976, abandoned.

[51] Int. Cl.² .................. A61B 17/06; A61B 19/00
[52] U.S. Cl. .................................. 206/370; 206/478; 206/483; 206/565; 206/571
[58] Field of Search ............ 150/52 C; 206/223, 329, 206/363, 370, 372, 473, 478, 480, 483, 44.12, 210, 214, 569, 570, 571, 572, 565, 566, 587, 593, 493, 474, 339, 332; 229/16 C

[56] References Cited

U.S. PATENT DOCUMENTS

| | | | |
|---|---|---|---|
| 1,565,389 | 12/1925 | Peacock | 150/52 C |
| 1,731,007 | 10/1929 | Graffenberger | 229/16 C |
| 1,776,295 | 9/1930 | Shields | 206/214 |
| 1,980,141 | 11/1934 | MacGregor | 206/593 |
| 3,032,182 | 5/1962 | Bechtold | 206/439 |
| 3,137,387 | 6/1964 | Overment | 206/370 |
| 3,180,485 | 4/1965 | Nevitt | 206/572 |
| 3,631,973 | 1/1972 | Rode | 206/593 |
| 3,749,233 | 7/1973 | McCormick, Jr. | 150/52 C |

FOREIGN PATENT DOCUMENTS 954608  4/1964  United Kingdom .................... 206/553

Primary Examiner—Herbert F. Ross
Attorney, Agent, or Firm—Kane, Dalsimer, Kane, Sullivan & Kurucz

[57] ABSTRACT

A strip tray for holding medical instruments during shipment, storage and use. The tray includes a strip of flexible material with receptacles on the strip for positioning medical instruments in a predetermined arranged pattern. The strip is adapted to be closed with the medical instruments contained therein protective position for shipment and storage. Furthermore, the strip is adapted to be opened and permit ready access to the medical instruments for use. Finally, the strip is adapted to be mounted to a protective covering which operates in cooperation with the strip when the strip is opened and closed.

11 Claims, 11 Drawing Figures

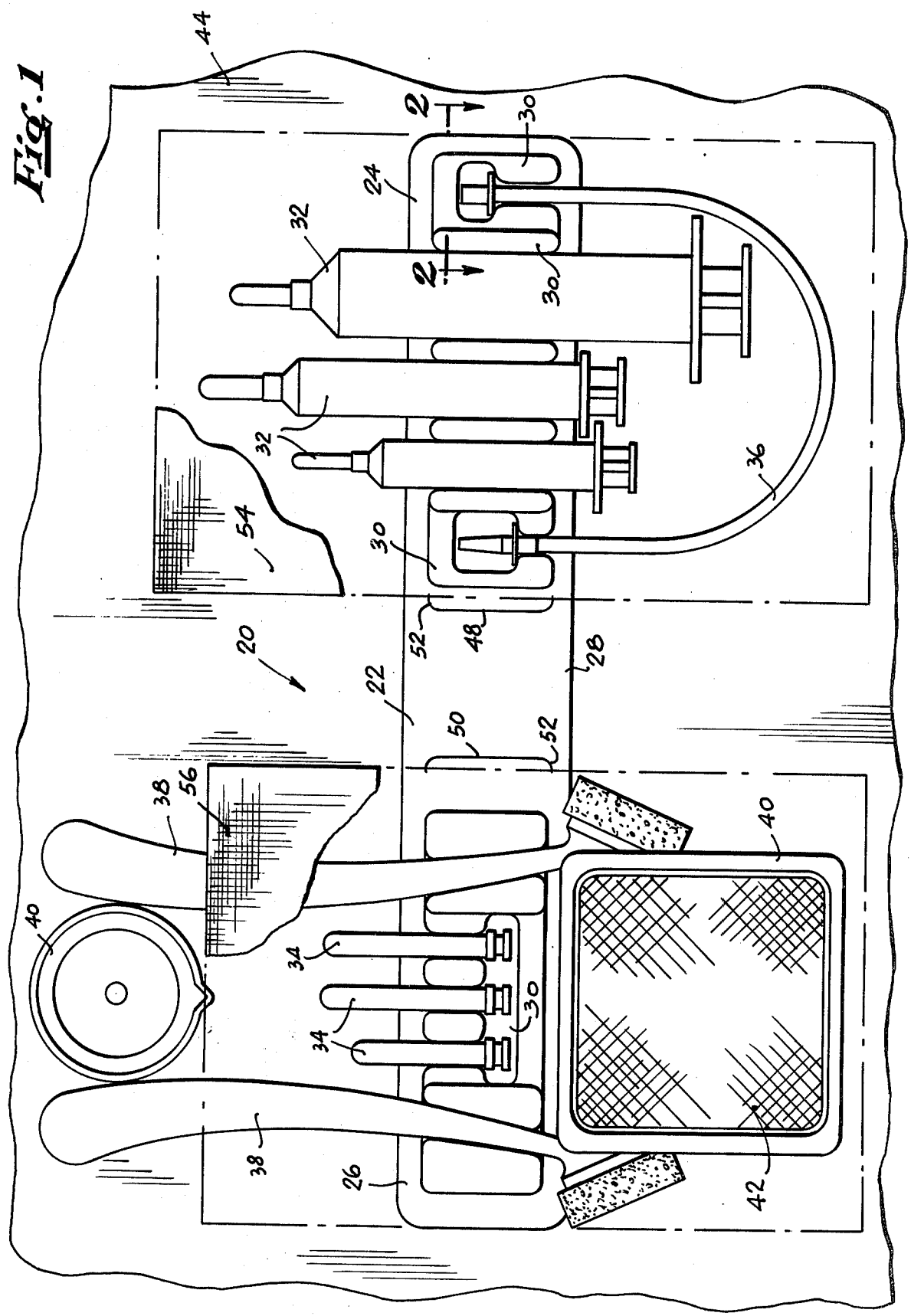

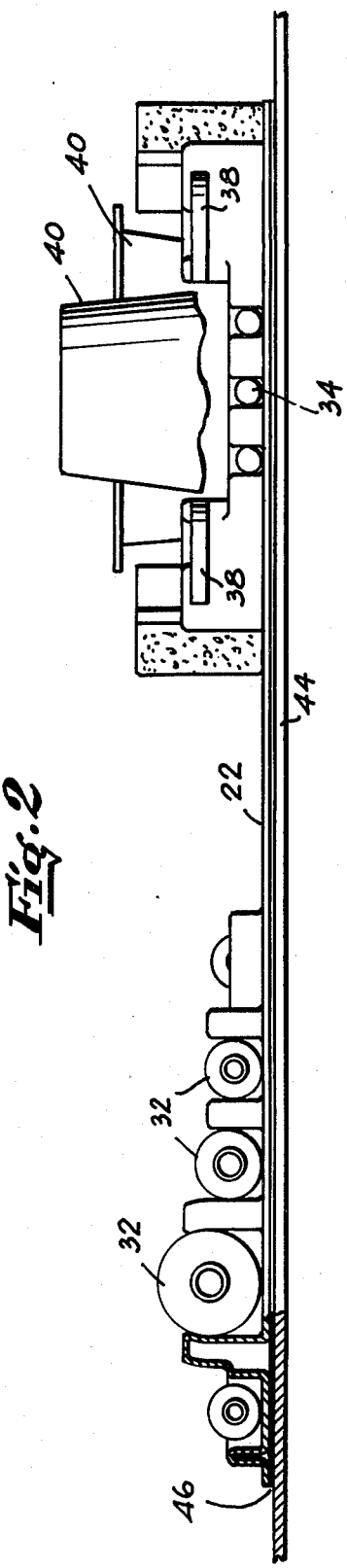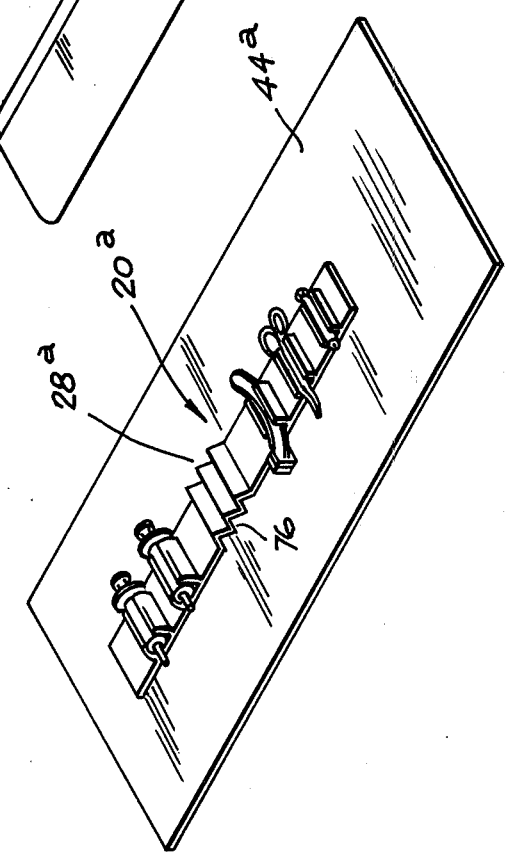

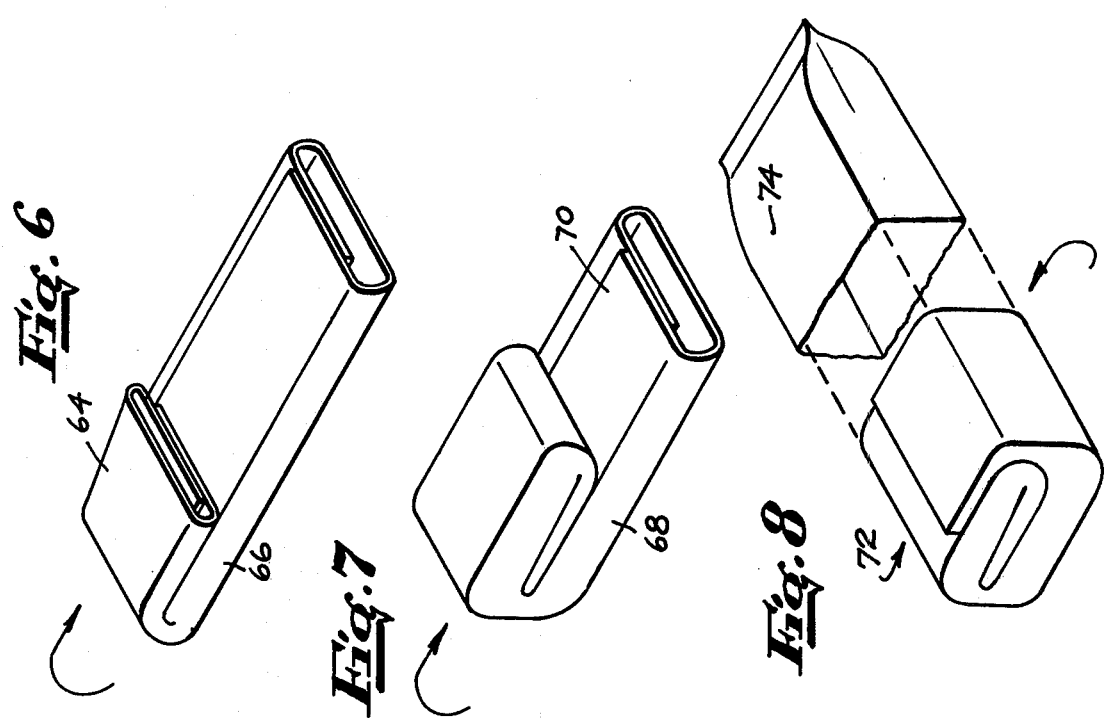
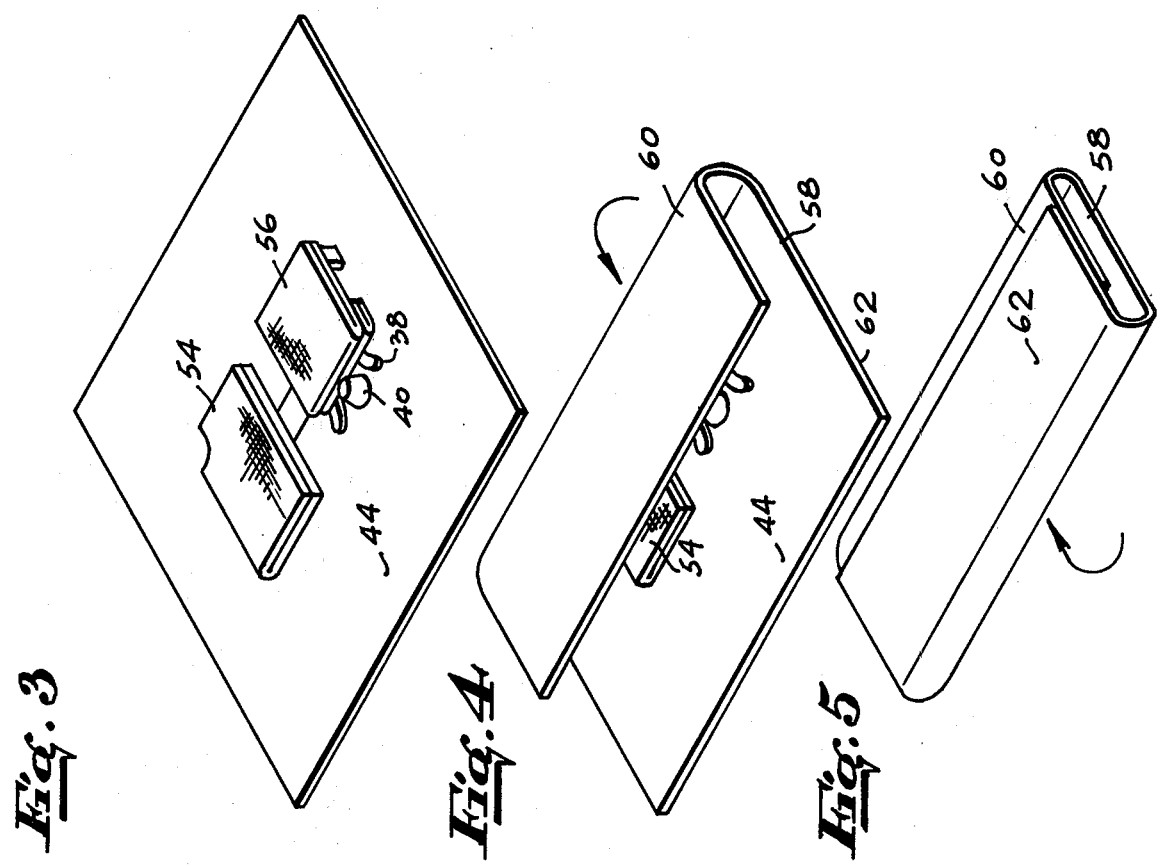

STRIP TRAY

This is a continuation of application Ser. No. 692,357, filed June 3, 1976, now abandoned.

BACKGROUND OF THE INVENTION

In medical procedures it is common today to provide kits of equipment which are designed to perform a particular procedure or operation and than to be disposable thereafter. In many of these kits, they are housed in rigid trays which are difficult to store and handle. Furthermore, it is often necessary to rigidly mount the instruments to prevent damage during shipping and handling prior to use. Naturally when the instruments are mounted in rigid fixed position, when the tray is open for use, it is often inconvenient, difficult and time consuming to gain access to the instruments when they are needed and to position them in their proper sequence for an efficient operation.

Rigid supporting tray elements and associated devices for protecting the instruments are often costly to manufacture and detract from the enjoyment of disposability after single use. Furthermore, there is also room for versatility in design and incorporation of other supporting structures such as protective drapes as part of the kit in order to improve the cost reduction of the overall system.

The types of procedures which lend themselves to this type of package tray arrangement are milogram, arthrogram, and angiogram and other similar medical procedures.

SUMMARY OF THE INVENTION

With the above background in mind, it is among the primary objectives of the present invention to provide a strip tray for medical procedures such as milogram, arthrogram and angiogram procedures. The tray is of low cost and minimum number of parts which lends itself to ready disposability. It also presents the products in a convenient registration arrangement for use. It protects the medical instruments during shipping and storage as well as providing a more compact package in non-use. The system is designed to be easily and inexpensively manufactured such as by the vacuum molding of a thermoplastic such as polystyrene or polypropylene and has means on the structure to facilitate the folding and unfolding of the tray with the medical instruments in proper position both for storage and for use.

The tray is designed to be associated with a protective covering or drape which helps in forming a cushion to protect the medical instruments during non-use and forms a background sterile surface for the instruments when the tray is unfolded for use. The tray is provided with specific holders to hold the medical instruments in position and also includes holders which are clip-like and more versatile in that they facilitate interchangeability of components. Furthermore, the design of the tray is such that certain of the medical instruments are packaged to facilitate their use as additional support members and cushioning members.

It is also an objective of the present strip tray to retain the medical instruments in fixed registered position during the folded condition for shipping and storage and in the proper registered condition for use after the tray has been unfolded and the instruments are to be utilized.

The tray is designed for cooperation with the drape which is folded in a manner to provide the desired cushioning and protective effect for the medical instruments and which can be easily unfolded into the flat background condition with the medical instruments exposed for ready access and use.

The entire folded package of tray and covering material is designed for ease of packaging in a heat sealed bag and sterilized therein in ready to use condition.

Embodiments are envisioned where the tray is designed for folding between the open and close position or, alternatively, rolling between the open and close positions. Also it is contemplated that an arrangement of instruments can be provided where there are more than two layers of instruments in registration when the tray is folded.

In summary, a strip tray is provided for holding medical instruments during shipment, storage and use. The tray includes a strip of flexible material with receptacles on the strip for positioning medical instruments in a predetermined protective arrangement. Means is on the strip to permit the closing of the strip with the medical instruments contained therein in protected condition for shipment and storage and to permit the strip to be opened for ready access to the medical instrument during use. Finally, means is on the strip for mounting the strip to a protective covering in cooperating relationship therewith when the strip is opened and closed.

With the above objectives among others in mind, reference is made to the attached drawings.

BRIEF DESCRIPTION OF THE DRAWINGS

In the drawings:

FIG. 1 is a top plan view of the strip tray of the invention with instruments mounted in position thereon and the tray mounted on a fragmentary portion of a protective covering;

FIG. 2 is a sectional view thereof taken along the plane of line 2—2 of FIG. 1;

FIGS. 3-8 show the sequence of folding the tray including instruments and protective covering into the close position and then insertion of the closed package into a sterile container;

FIGS. 9-11 show an alternative form of the strip tray and a protective covering associated therewith and the method of folding and rolling the alternative form into the closed position.

DESCRIPTION OF THE PREFERRED EMBODIMENTS

Strip tray 20 is basically strip 22 of flexible material which consists of three sections. There are two end sections 24 and 26 which are spaced by a central section 28. When folded, end section 24 registers with the other end section 26 and central section 28 forms the hinge for the folding and unfolding of the tray. FIGS. 1 and 2 show the tray in the unfolded condition.

Each of the end sections 24 and 26 include a plurality of preformed receptacles 30 which are designed to hold certain types of medical instruments. The receptacles can be integrally formed with the remainder of the tray by a conventional process such as vacuum molding. In the depicted embodiment of FIGS. 1-8, the tray shown is designed for a knee arthrogram procedure and includes the appropriate instruments for that purpose. For example, a number of syringes 32 are included along with a number of needles 34, appropriate tubing 36, applicators 38, cups 40 and gauze padding 42.

The receptacles 30 for holding most of the elements including the needles and the applicators are clip-like receptacles which resiliently expand upon insertion of the instrument and then grasp the instrument to assist in retaining it in position. By providing clip-like resilient receptacles, it is possible to accommodate differences in sizes for the medical instruments and, accordingly makes, interchangeability of instruments available. The receptacle 30 holding the syringe 32 can be clip-like but is preferably rigid with an arcuate configuration to fit the syringe barrel. This is due to the fact that in procedural practice, it has been found to be an advantage to have the syringes very easily removable from their holders for use.

The strip is essentially mounted on a larger protective covering or drape 44 which can be of paper of cloth material. The drape 44 forms a sterile background for the instruments when the tray is in the open position as shown in FIG. 1 and also facilitates folding of the tray into the closed position during which it acts as a protective padding for the instruments held within as well as assisting in retaining the instruments in position.

The strip tray 20 is mounted to the drape 44 in a conventional fashion such as by the use of a double sided adhesive tape 46.

The folding of the strip tray is facilitated by a pair of die cuts 48 and 50 in the central portion 28. The die cuts form a weakened zone and enables end section 24 to be easily folded into registration within section 26. The ends of the die cuts are formed with arcuate portions 52 which guards against tearing of the strip during folding and unfolding.

In assembly, as discussed above, the strip tray 20 can be vacuum formed as a unitary element with receptacles 30 therein and then die cuts 48 and 50 can be formed. The number of die cuts is a matter of choice with two being the number shown in the depicted embodiment. The strip is then mounted to the drape 44 by means of the double sided tape 46 and the appropriate instruments are positioned in the receptacles as shown in FIGS. 1 and 2.

FIGS. 3-8 then show the steps of folding and packaging the strip tray. Initially paper or cloth towels 54 and 56 can be positioned on the open tray with the instruments therein as further protective padding. This arrangement is depicted in FIG. 3. The first folding steps are depicted in FIGS. 4 and 5 where the drape 44 is folded into thirds with the fold edges being aligned with the longitudinal axis of the strip tray. The center fold 58 contains the strip tray 20 and the overlapping folds 60 and 62 form coverings.

The strip tray and drape is then folded four times in a direction parallel with the lateral axis of the strip tray as shown in FIGS. 6 and 7 until it reaches the final folded condition as shown in FIG. 8. During the folding sequence the first fold of the drapw 64 forms padding for the second fold 66 which contains the one end section of the strip tray the third fold 68 contains the other end section of the strip tray which is thus in registration with the first end section and the fourth fold 70 forms additional padding for the folded strip tray and also provides a compact finished closed tray assembly 72. The assembly can than be inserted into a bag 74 which can be heat sealed and the entire package sterilized for shipment and storage.

In use, it can be readily seen how the process of FIGS. 3-8 can be easily reversed when the tray is to be used. It can be quickly and efficiently unpackaged and then unfolded to the open position of FIGS. 1-3 with drapw 44 forming a sterile background on which the medical instruments are displayed for use.

FIGS. 9-11 show an alternative form of the strip tray 20a with the difference residing in the manner in which the strip is shifted between the open and closed positions. It is mounted in the same manner to a drape 44a and holds the instruments in the same fashion as well. The difference in structure resides in the central section 28a where, in place of the die cuts, a series of corrugations 76 are provided. These corrugations permit the tray 20a to be rolled in the closed configuration rather than folded. The sequence of closing is depicted in FIGS. 10 and 11. Drape 44a is folded into thirds with the fold lines being parallel to the longitudinal axis of the strip tray 20a and then the elongated arrangement of FIG. 10 with the drape forming a cushion for the instruments is rolled as shown in FIG. 11 into the fully closed position. It then can be stored in a sterile bag in the same manner as in the previously discussed embodiment.

In both embodiments appropriate portions of the stored medical instruments can act as spacers to provide additional support for the packaged tray and alleviate the danger of damage occuring to the instruments. Additional vertical support can be provided, for example, by cups 40 which form vertical rigid spacers since the cups are formed of a rigid plastic disposable material.

The strip tray is disposable and of low cost construction, presents the medical instruments in convenient registration for use as well as retaining the instruments from loosely flopping around in the package. The closed tray is compact in non-use and the strip tray is adaptable for use in many medical procedures such as milogram procedures, arthrogram procedures and angiogram procedures.

The sterilization of the packaged unit can be accomplished in conventional ways such as by carbon dioxide or radiation sterilization.

The material for drape 44 can be a water-proof cloth or paper material or other conventional type of similar material which creates a soft sterile background field.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A strip tray for holding medical instruments during shipment, storage and use comprising; an elongated narrow strip of material, receptacles on the strip for positioning medical instruments in a predetermined arrangement, means on the strip including weakened zones to permit the closing of the strip along fold lines substantially perpendicular to the longitudinal axis with the medical instruments contained thereon in protected position for shipment and storage and to permit the strip to be opened for ready access to the medical instruments in the predetermined arrangement during use, and means on the strip for mounting the strip to a protective covering substantially larger in area than the strip in cooperating relationship therewith when the strip is opened and closed, the strip containing a support section including a number of spaced projections along its length, a wall of each projection combining with the facing wall of an adjacent projection and the adjoining portion of the support section therebetween at the base of the walls to form an open cavity, the cavities being in a predetermined arrangement to receive the medical instruments in the desired position thereon with an instrument in each cavity for immediate and sequential operative use and to facilitate the retention of the instruments in that position during opening and closing of the strip when adjacent projections will be directed toward one another to decrease the size of the cavity therebetween in order to facilitate holding of the instruments while not interfering with quick and easy access to the instruments during use when the strip is open and the projections will separate permitting free access to the instruments for removal and use, the protective covering being in the form of a drape and the strip adapted to be mounted on the drape in position to hold the medical instruments exposed in proper array for immediate unencumbered access and use when the drape is open to form a protective background for the instruments, and the drape facilitating the closing of the strip and easily conforming to the shape of the closed strip so as to form a protective covering to assist in retaining the instruments in position during shipment and storage, the plastic strip being provided with at least one lateral die cut positioned with respect to the instruments contained on the strip so as to facilitate the folding and unfolding of the strip, a group of receptacles for receiving the medical instruments on one side of the die cut and a group of receptacles for receiving medical instruments on the other side of the die cut so that when the strip is folded the die cut will permit the medical instruments on one side thereof to register with the medical instruments on the other side thereof, each die cut terminating in curved ends to facilitate the prevention of cracking and failure of the strip during folding and unfolding procedures.

2. The invention in accordance with claim 1 wherein the strip is mounted to a protective covering by means of a double sided adhesive tape with one side adhered to the strip and the other side adhered to the protective covering, the strip of flexible material being formed of a thermo plastic material.

3. The invention in accordance with claim 1 wherein there are a pair of spaced lateral die cuts on the strip and located in the central portion of the strip, a group of receptacles for receiving the medical instruments on one side of the die cuts and a group of receptacles for receiving medical instruments on the other side of the die cuts so that when the strip is folded the die cuts will permit the medical instruments on one side thereof to register with the medical instruments on the other side thereof.

4. The invention in accordance with claim 2 wherein the strip is mounted in a central location on the drape, the drape being foldable into three parts parallel to the axial direction of the strip and then into four parts perpendicular to the lateral direction of the strip to provide a protective covering for the strip and medical instruments as well as protective cushioning for the medical instruments and the drape being adapted to be readily unfolded with the strip to form a sterile background on the strip containing the medical instruments in unfolded condition ready for use.

5. The invention in accordance with claim 4 wherein rigid spacers are provided perpendicular to the plane of the strip to facilitate protection of the medical instruments, the spacers being rigid and being formed by parts of the medical instruments, and cushioning surgical napkins folded within the drape and strip in protective arrangement with respect to the medical instruments to provide additional protective cushioning for the instruments when in the folded condition.

6. The invention in accordance with claim 1 wherein the strip is adapted to be rolled into the closed position and unrolled into the open position.

7. The invention in accordance with claim 1 wherein the strip tray is formed to include the medical instruments required for knee arthrogram tray.

8. The invention in accordance with claim 1 wherein the receptacles include clip-like holders for receiving certain of the medical instruments and preformed rigid wells to receive other of the medical instruments and to permit ease of removal of the instruments for use.

9. The invention in accordance with claim 1 wherein the strip tray when in the closed position in packaged within a sterile sealed container to protect the sterile condition of the instruments contained therein during shipment and storage and prior to use.

10. A strip tray for holding medical instruments during shipment, storage and use comprising; a strip of flexible material, receptacles on the strip for positioning medical instruments in a predetermined arrangement, means on the strip to permit the closing of the strip with the medical instruments contained thereon in protected position for shipment and storage and to permit the strip to be opened for ready access to the medical instruments in the predetermined arrangement during use, means on the strip for mounting the strip to a protective covering in cooperating relationship therewith when the strip is opened and closed, the strip being adapted to be rolled into the closed position and unrolled into the open position, the means for facilitating rolling of the strip including a plurality of corrugations intermediate the ends of the strip with one group of medical instruments being held in receptacles on one side of the corrugations and a second group of medical instruments being held in receptacles on the other side of the corrugations.

11. The invention in accordance with claim 10 wherein the protective covering is in the form of a drape adapted to be folded along fold lines parallel to the axial length of the strip and then rolled in a direction parallel to the lateral axis of the strip to provide a protective covering for the strip when folded and a protective background for the strip and medical instruments when unfolded for use.

* * * * *